United States Patent
Goldbach

(10) Patent No.: US 9,622,824 B2
(45) Date of Patent: Apr. 18, 2017

(54) METHOD FOR AUTOMATICALLY IDENTIFYING INSTRUMENTS DURING MEDICAL NAVIGATION

(75) Inventor: Günter Goldbach, Wörth/Wifling (DE)

(73) Assignee: Brainlab AG, Munich (DE)

( * ) Notice: Subject to any disclaimer, the term of this patent is extended or adjusted under 35 U.S.C. 154(b) by 2668 days.

(21) Appl. No.: 11/766,954

(22) Filed: Jun. 22, 2007

(65) Prior Publication Data

US 2008/0021311 A1   Jan. 24, 2008

Related U.S. Application Data

(60) Provisional application No. 60/806,508, filed on Jul. 3, 2006.

(30) Foreign Application Priority Data

Jun. 23, 2006 (EP) .................................... 06013010

(51) Int. Cl.
| | | |
|---|---|---|
| A61B 19/00 | (2006.01) | |
| A61B 34/20 | (2016.01) | |
| A61B 17/00 | (2006.01) | |
| A61B 90/00 | (2016.01) | |

(52) U.S. Cl.
CPC ............. *A61B 34/20* (2016.02); *A61B 90/39* (2016.02); *A61B 2017/00725* (2013.01); *A61B 2034/2055* (2016.02); *A61B 2090/3983* (2016.02)

(58) Field of Classification Search
USPC ............. 600/407, 410, 414, 417, 424, 426; 606/130
See application file for complete search history.

(56) References Cited

U.S. PATENT DOCUMENTS

| | | | |
|---|---|---|---|
| 6,527,443 B1 * | 3/2003 | Vilsmeier | A61B 6/12 378/205 |
| 6,782,288 B2 * | 8/2004 | Truwit et al. | 600/429 |
| 2005/0085714 A1 * | 4/2005 | Foley et al. | 600/424 |
| 2005/0197569 A1 * | 9/2005 | McCombs | 600/426 |
| 2005/0215888 A1 | 9/2005 | Grimm et al. | |
| 2005/0228270 A1 * | 10/2005 | Lloyd et al. | 600/424 |
| 2005/0267358 A1 | 12/2005 | Tuma et al. | |
| 2005/0267360 A1 * | 12/2005 | Birkenbach | A61B 90/36 600/423 |

(Continued)

FOREIGN PATENT DOCUMENTS

| | | |
|---|---|---|
| DE | 19 639 615 | 4/1998 |
| DE | EP 1033113 A1 * | 9/2000 |

(Continued)

*Primary Examiner* — Rochelle Turchen
(74) *Attorney, Agent, or Firm* — Tucker Ellis LLP

(57) ABSTRACT

A method for using a medical navigation system to identify an instrument to be navigated is provided, wherein the instrument includes a reference array having a plurality of markers that form a rigid body, and a location of the markers with respect to each other is not previously known in the navigation system as a characteristic arrangement for a particular instrument. The method includes measuring a distance of each marker relative to the other markers; identifying a spatial arrangement of the markers having the measured distance as an assignable marker array; assigning the assignable marker array to the instrument; and identifying the instrument based on the assigned marker array.

19 Claims, 2 Drawing Sheets

(56) References Cited

U.S. PATENT DOCUMENTS

2006/0189867 A1* 8/2006 Revie et al. .................. 600/424
2007/0073137 A1* 3/2007 Schoenefeld ................. 600/407

FOREIGN PATENT DOCUMENTS

| EP | 1 563 799 | 2/2004 |
|----|-----------|--------|
| WO | 01/54558 | 8/2001 |
| WO | 2005/067794 | 7/2005 |

* cited by examiner

METHOD FOR AUTOMATICALLY IDENTIFYING INSTRUMENTS DURING MEDICAL NAVIGATION

RELATED APPLICATION DATA

This application claims priority of U.S. Provisional Application No. 60/806,508 filed on Jul. 3, 2006, which is incorporated herein by reference in its entirety.

FIELD OF THE INVENTION

The invention relates to a method and system for identifying an instrument, such as a navigated medical instrument.

BACKGROUND OF THE INVENTION

Medical navigation systems are known and used to provide operating physicians with visual assistance during operations. Such visual assistance may include indicating a location of positionally determined and tracked instruments with respect to particular parts of the patient's body. The information concerning the body parts can be previously or intra-operatively ascertained using imaging methods. Further, with the aid of an initial registration procedure, the spatial positions of the patient, the corresponding image data and the instruments used in the operating theater can be assigned such that navigation and/or image-assisted surgery can be subsequently performed. An exemplary navigation system is described in DE 19 639 615 C2.

A fundamental concept of such image-guided surgery systems that use a spatial arrangement of marker elements may be based on the arrangement of marker elements (e.g., a reference array that includes one or more marker elements) on instruments, patients or treatment-assisting apparatus. The spatial arrangement of marker elements, which are formed as rigid bodies, may be used in a defined coordinate system or may define the coordinate system. More specifically, these rigid marker bodies can be translated into a reference system, compared with a reference system that is predetermined by a reference set-up, or compared with an absolute position as defined by a tracking system.

Alternatively, geometries of the spatial arrangement of marker elements may be predefined and stored in the navigation system. This can apply to navigation systems in accordance with the above-referenced document or also to other navigation and/or tracking systems (optical tracking systems, magnetic tracking systems, ultrasound tracking systems, etc.). In other words, a number of different and characteristic spatial arrangements of marker elements may be previously known to and/or stored in the navigation system, wherein the characteristic spatial arrangements of marker elements each correspond to a particular reference array (group of marker elements) or are already assigned to an instrument.

Further, the geometry of the instrument also may be stored in the navigation system. If the navigation system, via data obtained from the tracking system, identifies one or more particular and characteristic spatial arrangements of marker elements, the one or more spatial arrangements of marker elements can be compared with the previously stored spatial arrangements of marker elements. If these previously stored spatial arrangements of marker elements are each associated with a particular instrument or reference array, then the instrument and/or reference array also can be identified. In such systems, it is preferable that the rigid geometries defined by the spatial arrangement of marker elements have a high degree of accuracy. This enables the spatial arrangement of marker elements to be properly identified, as well as enabling the calculation of six degrees of freedom (three-dimensional position +orientation on the three spatial axes) for localizing the instrument.

SUMMARY OF THE INVENTION

A method for identifying an instrument for navigation using a medical navigation system is provided, wherein the instrument includes, for example, a reference array that comprises a number of marker elements (A, B, C). The arrangement of the marker elements on the reference array forms a rigid body, wherein the location of the marker elements with respect to each other is not known in the navigation system as a characteristic spatial arrangement for a particular instrument, wherein the method includes:

a distance of the marker elements (A, B, C) from each other is measured, for example, using a medical optical tracking system that is assigned to the navigation system;
  a spatial arrangement of marker elements having the measured distance for the marker elements is identified as an assignable spatial arrangement of marker elements;
  the spatial arrangement of marker elements is assigned to the instrument and the instrument is identified by the navigation system.

Using currently available tracking systems and, preferably highly dynamic tracking systems, it is possible to calculate relative distances of the identified marker elements coupled to the instrument (provided the marker elements are in the visual field of the tracking system). This includes calculating distances of moving marker geometries. The systems and, in particular, the highly dynamic systems, are fast enough to detect the spatial positions of the marker elements within a predetermined accuracy. Further, the systems can detect faster than typical movements of the instrument during use. While such highly dynamic systems are preferred, they are not essential for implementing the method.

When the marker elements form a rigid body in their arrangement on the reference array, they will always have the same distance from each other, even when the instrument, the reference system or the tracking system is moved. On this basis, it is possible to identify the rigid bodies by producing a movement with respect to the tracking system or with respect to other instruments that have already been identified. Then, based on the spatial arrangement of marker elements forming a rigid body, the instrument and/or the spatial arrangement of marker elements can be identified as an assignable spatial arrangement of marker elements. In other words, the detected rigid body is no longer compared with predefined, known marker geometries stored in the navigation system, but rather the rigid bodies that form the marker geometries are determined and/or identified by measuring the relative positions and/or distances of the marker elements. The method thus acknowledges a spatial arrangement of marker elements introduced into the visual field of the tracking system just as it is, and classifies it as an assignable and specific marker configuration or marker geometry that then can be assigned to an instrument.

It thus becomes possible, for example, to use a large number of different rigid body marker geometries, without having to store them in a database beforehand. Since the marker geometries need not correspond to the parameters of known, stored and/or identifiable marker geometries in the navigation system, it is possible to also use inaccurately produced and cost-effective instruments provided with marker elements, since the exact distance between the marker elements is no longer relevant to identifying the instrument. The only assumption for identification is that the marker rigid body geometry does indeed remain a rigid body while the surgeon is using the instrument.

The method can significantly improve and/or protract the reliability and applicability of surgical navigation systems and/or image-guided surgery systems due to the smaller demands on their production accuracy and/or the enduring shape of the instrument. Another advantage of the absence of demands on production tolerances is that disposable instruments that are relatively cheap to produce can be used in highly critical applications such as, for example, in Creutzfeldt-Jakob diseases. The same applies to applications that are to be realized on a low budget, e.g., wherein sterilizing the instruments is not affordable.

In one embodiment, the instrument can be moved while measuring the relative distance between the marker elements so as to identify the spatial arrangement of marker elements. The tracking system can also be moved relative to the spatial arrangement of marker elements. In other words, the method can look at a relative movement between the spatial arrangement of marker elements and the tracking system.

The positional relationship between the functional portion of the instrument, such as the tip of the instrument, and the spatial arrangement of marker elements can be determined by moving the instrument while the functional portion and/or tip is fixed. This positional relationship can be determined by tracking the marker elements, wherein the positional relationship can be defined as a spatial relationship of the rigid body of marker elements and the functional portion (e.g., tip) of the instrument. Further, the distance can be measured while the positional relationship is determined or after it has been determined. If the tip and/or functional portion of the instrument is fixed, the marker elements will perform a circular or spherical movement about the tip. The center of this circular or spherical movement can be ascertained, since the trajectories of the marker elements also may be ascertained via the tracking system. It is therefore not necessary for the spatially fixed point about which the movement is performed to be known with respect to its position. The instrument thus can be moved about a spatially unknown, spatially fixed point, which can be a spatially fixed positioning recess for the functional portion of the instrument, such as the tip of the instrument. While this positioning recess will allow the tip to be fixed, it allows the instrument to be moved.

If the position of the functional portion and/or tip of the instrument is ascertained, additional advantages and/or possible applications result. For example, instruments that have been slightly damaged or deformed but which can otherwise still fulfill their function still may be used. If surgical instruments change their geometry (due to heavy use, cleaning or sterilizing processes, or bending which can arise due to instruments being dropped or abused), they can continue to be used by using the identifying method described herein (e.g., by ascertaining the position of the functional portion and/or tip of the instrument after the measured spatial arrangement of marker elements has been identified and assigned to the instrument). As already mentioned, the method assumes the marker rigid body remains rigid while the instrument is in use and does not move with respect to the instrument. Since the marker geometries are not stored in the navigation system but are rather only ascertained when the instrument is used and/or when beginning to use the instrument, it is impossible for predefined spatial arrangement of marker elements to be assigned to an instrument that no longer corresponds with stored data (e.g., an instrument whose geometry has been altered due to use) and, thus, errors are avoided. For this reason, it is possible to use instruments that have had geometrical data and/or marker geometry stored in a database but which, due to deformations or production errors, now have different geometries from that stored in the database.

When implementing the method, the aforementioned spatially fixed point also can be a registration landmark on a patient or treatment-assisting apparatus. If this is the case, the instrument can be identified and/or the distance measured and/or the positional relationship determined when a landmark is registered by the instrument, such that up to three steps can be completed at once.

The functional portion of the instrument and/or the tip of the instrument can be determined, for example, by pivoting movements about a spatially fixed point. The location of the tip relative to the marker array and/or marker geometry also can be determined by using an instrument calibration matrix, which is an apparatus that provides contact locations (points, lines, areas) for instruments, at which the latter can be registered.

Also provided herein is a program which, when it is running on a computer or is loaded onto a computer, causes the computer to perform a method as described herein. The computer program may be stored on a computer readable medium, for example.

BRIEF DESCRIPTION OF THE DRAWINGS

The forgoing and other features of the invention are hereinafter discussed with reference to the drawings.

DETAILED DESCRIPTION

Figure 1:
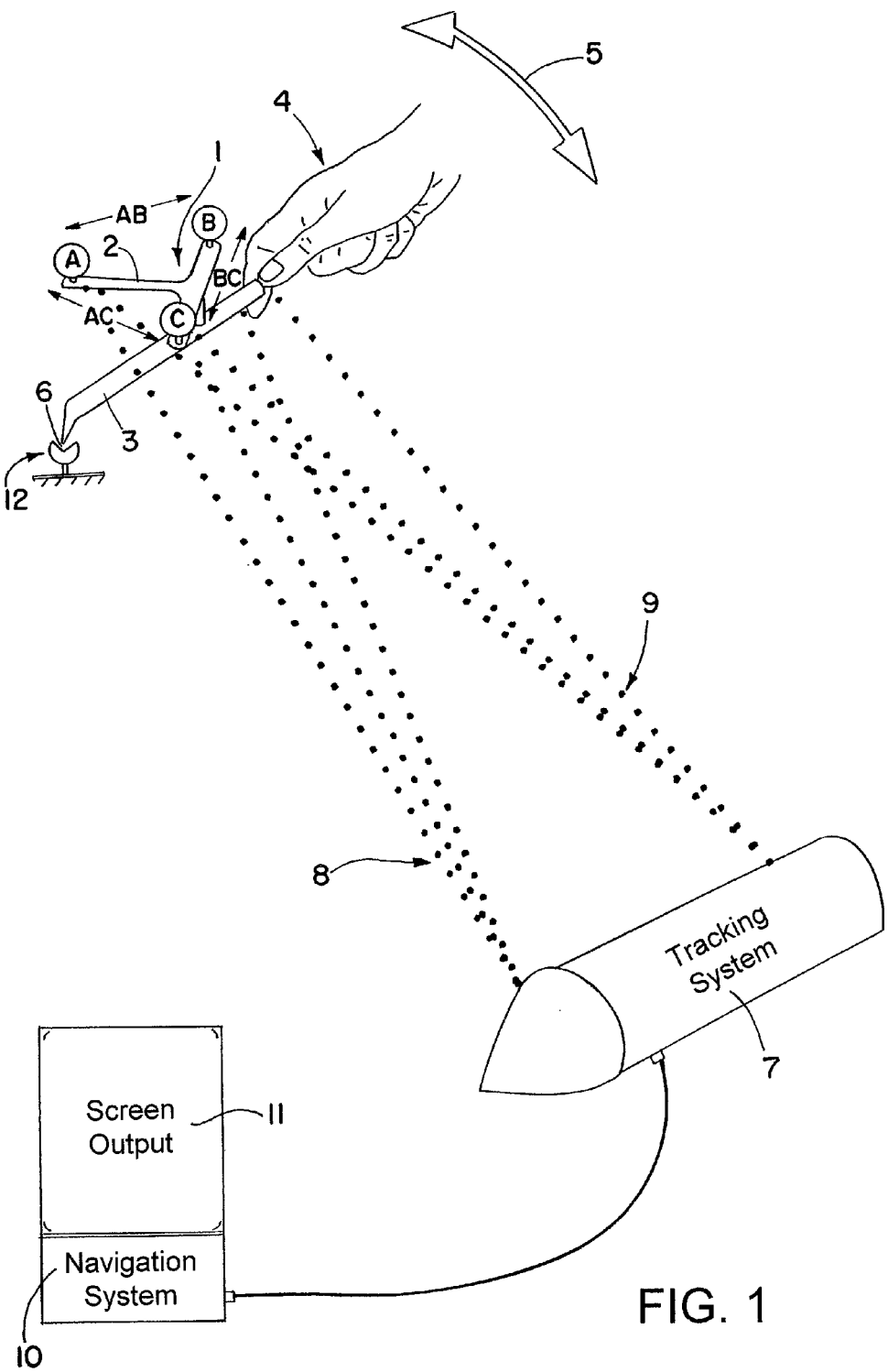
FIG. 1 illustrates an exemplary instrument comprising a spatial arrangement of marker elements within the environment of a medical navigation and tracking system.

FIG. 1 illustrates an exemplary rigid body that includes marker elements, wherein the rigid body is identified by means of a navigation and/or tracking system. More specifically, the marker elements A, B, and C may be arranged on a reference array 1 via arms 2 and attached to an instrument 3, wherein the rigid body may be identified by moving the instrument 3 within the working range of the navigation system 10 and/or tracking system 7. While an optical tracking is shown, other tracking systems may be utilized, including, for example, ultrasound, magnetic or laser tracking and navigation systems.

The instrument 3 comprises a tip 6, and a spatial arrangement of the marker elements A, B, and C on the reference array 1 is fixed, such that the distances AB, AC and BC of the three marker elements form a rigid body and/or rigid marker body geometry. The distances AB, AC and BC can be detected by the tracking system 7, which can operate stereoscopically, i.e., using two cameras having lines of sight 8 and 9. Due to the stereoscopic scanning of the tracking system 7, it is possible to determine the absolute positions of the marker elements A, B and C as well as their respective distances. The tracking system 7 can be connected to the navigation system 10, which comprises a screen output 11 (the navigation system 10 and screen output 11 are only shown schematically). The navigation system 10 can receive and process the positional data ascertained by the tracking system 7, and display the data via the screen output 11 (also referred to as display 11) so as to provide image assistance. The navigation system 10 also may perform assignment and identification measures.

The embodiment shown indicates one way in which the position of the tip 6 of the instrument 3 can be detected. To this end, a positioning recess 12 can be provided for the tip of the instrument 3, wherein the recess may be arranged at a spatially fixed point. A location of the recess in three dimensional space, however, need not be known. In the present example, the recess 12 has a funnel-shaped cavity that allows the tip 6 to be fixed but still allows the instrument to move. In the present case, the movement is performed as a pivoting movement about the fixed tip 6, as indicated by the arrow 5. By measuring the distances between the marker elements A, B and C, this specific marker configuration having said specific relative distances of the marker elements can be identified as an assignable spatial arrangement of marker elements.

The rigid body predetermined by the marker geometry can be determined, for example, by performing a pivoting movement about the fixed tip 6, or beforehand during another movement of the instrument within the visual field of the tracking system 7. Since the marker elements A, B, and C move about the tip 6 in circular movements and/or movements on the surface of a sphere, the center of this movement also can be ascertained, said center being the position of the tip 6. The position of the spatial arrangement of marker elements can be assigned to the position of the tip 6, and the position of the tip 6 then is always known in the navigation system 10. After this process, the instrument 3 can continue to be navigated as a tracked instrument and used in image-assisted surgery, even though it has not been previously stored and/or identified in a data set of the navigation system 10.

A patient landmark or a marking point of a treatment-assisting instrument also could be selected instead of the positioning recess 12, such that said point could be simultaneously registered.

Using the above method, any instrument, even cost-effectively produced instruments that comprise rigid body marker arrangements, can be used for navigation and/or tracking. It is also possible to improve the accuracy of pre-calibrated tools, if the tolerances of theses tools due to production problems or attrition become critical.

Figure 2:
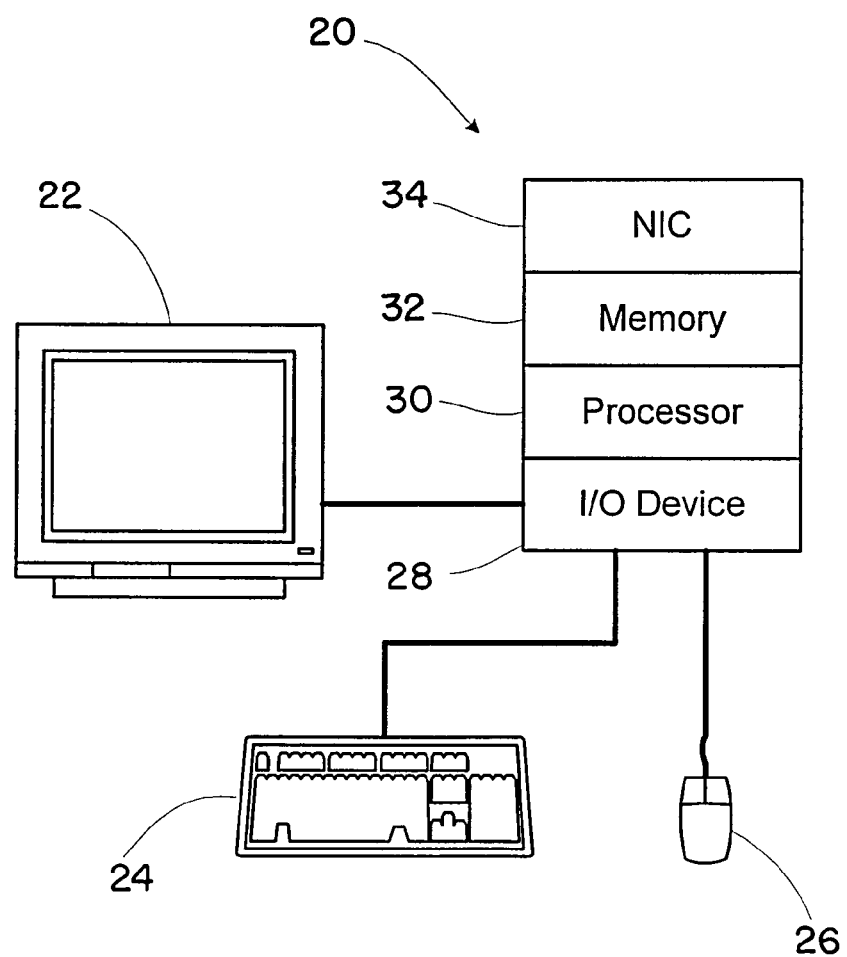
FIG. 2 is a block diagram of an exemplary computer system that can be used to carry out the method in accordance with invention.

FIG. 2 illustrates the exemplary computer system 20 that may be used to implement the method described herein (e.g., as a computer of the navigation system 10 and/or tracking system 7). The computer system 20 may include a display 22 for viewing system information (which may be in addition to the display 11, or may be the display 11), and a keyboard 24 and pointing device 26 for data entry, screen navigation, etc. A computer mouse or other device that points to or otherwise identifies a location, action, etc., e.g., by a point and click method or some other method, are examples of a pointing device 26. Alternatively, a touch screen (not shown) may be used in place of the keyboard 24 and pointing device 26. The display 22, keyboard 24 and mouse 26 communicate with a processor via an input/output device 28, such as a video card and/or serial port (e.g., a USB port or the like).

A processor 30, such as an AMD Athlon 64® processor or an Intel Pentium IV® processor, combined with a memory 32 execute programs to perform various functions, such as data entry, numerical calculations, screen display, system setup, etc. The memory 32 may comprise several devices, including volatile and non-volatile memory components. Accordingly, the memory 32 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 30 and the memory 32 are coupled together via a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 34 allows the computer system 20 to communicate with other devices.

A person having ordinary skill in the art of computer programming and applications of programming for computer systems would be able in view of the description provided herein to program a computer system 20 to operate and to carry out the functions described herein. Accordingly, details as to the specific programming code have been omitted for the sake of brevity. Also, while software in the memory 32 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for automatically assigning identification to an associated navigable medical instrument in a medical navigation system operatively coupled with a tracking system, the method comprising:

storing first geometrical data in a non-transitory memory of the tracking system or the medical navigation system, the first geometrical data being representative of first physical properties of the navigable medical instrument at a first time before a use time of the navigable medical instrument;

operating the tracking system at a second time before the use time to measure relative distances between each of at least three marker elements having a fixed mutual spatial relationship defining a rigid marker body geometry on a reference array coupled with the navigable medical instrument;

assigning, by the tracking system or the medical navigation system, the reference array to the navigable medical instrument by associating in the non-transitory memory of the tracking system or the medical navigation system the measured relative distances with the first geometrical data of the navigable medical instrument;

determining, by the tracking system, positional data representative of a position of the rigid marker body geometry relative to the tracking system, and providing the determined positional data to the medical navigation system;

displaying on an output of the medical navigation system in accordance with the determined positional data an image of a position of the navigable medical instrument having the first physical properties and being assigned to the reference array;

storing, at a third time after the use time of the navigable medical instrument, second geometrical data in the non-transitory memory of the tracking system or the medical navigation system, the second geometrical data being representative of second physical properties of the associated navigable medical instrument changed from the first physical properties to the second physical properties in accordance with the navigable medical instrument being deformed from the first physical properties to the second physical properties;

operating the tracking system at a fourth time after the use time to re-measure the relative distances between each of the least three marker elements having the fixed mutual spatial relationship defining the rigid marker body geometry on the reference array coupled with the deformed navigable medical instrument;

assigning, by the tracking system or the medical navigation system, the reference array to the deformed navigable medical instrument by associating in the non-transitory memory of the tracking system or the medical navigation system the re-measured relative distances with the second geometrical data of the deformed navigable medical instrument;

determining, by the tracking system, positional data representative of a position of the rigid marker body geometry relative to the tracking system, and providing the positional data to the medical navigation system; and displaying on the output of the medical navigation system in accordance with the positional data an image of a position of the deformed navigable medical instrument having the second physical properties and being assigned to the reference array.

2. The method according to claim 1, wherein the operating the tracking system at the fourth time to measure the relative distances between each of the at least three marker elements comprises:

re-measuring the relative distances between each of the at least three marker elements while one of the associated deformed navigable medical instrument or the tracking system is moved relative to the other of the associated deformed navigable medical instrument or the tracking system.

3. The method according to claim 1, further comprising:

determining a positional relationship between a functional portion of the associated deformed navigable medical instrument and the reference array.

4. The method according to claim 3, wherein the determining the positional relationship between the functional portion of the associated deformed navigable medical instrument and the reference array comprises:

operating the tracking system to track the at least three marker elements as the associated deformed navigable medical instrument is moved while the functional portion remains at a fixed location.

5. The method according to claim 3, wherein the determining the positional relationship between the functional portion of the associated deformed navigable medical instrument and the reference array comprises:

operating the tracking system to track the at least three marker elements as the associated deformed navigable medical instrument is moved while a tip of the associated deformed navigable medical instrument remains at a fixed location.

6. The method according to claim 3, wherein:

the operating the tracking system to re-measure the relative distances between each of the at least three marker elements and the determining, by the tracking system or the medical navigation system, the positional relationship between the functional portion of the associated deformed navigable medical instrument and the reference array are performed simultaneously.

7. The method according to claim 3, wherein:

the operating the tracking system to re-measure the relative distances between each of the at least three marker elements is performed after the determining, by the tracking system or the medical navigation system, the positional relationship between the functional portion of the associated deformed navigable medical instrument and the reference array.

8. The method according to claim 3, wherein:

the determining the positional relationship between the functional portion of the associated deformed navigable medical instrument and the reference array comprises using an instrument calibration matrix storing data representative of a shape of the associated deformed navigable medical instrument.

9. The method according to claim 3, wherein the determining the positional relationship between the functional portion of the associated deformed navigable medical instrument and the reference array comprises:
   moving the associated deformed navigable medical instrument about a spatially fixed point.

10. The method according to claim 9, wherein the moving the associated deformed navigable medical instrument about the spatially fixed point comprises:
    moving the associated deformed navigable medical instrument about an unknown spatially fixed point.

11. The method according to claim 9, wherein the moving the associated deformed navigable medical instrument about the spatially fixed point comprises:
    providing a spatially fixed positioning recess; and
    disposing the functional portion of the associated deformed navigable medical instrument in the recess.

12. The method according to claim 9, wherein the moving the associated deformed navigable medical instrument about the spatially fixed point comprises:
    moving the associated deformed navigable medical instrument about a registration landmark on an associated patient or about a treatment-assisting apparatus as the spatially fixed point.

13. The method according to claim 3, wherein:
    the re-measuring the relative distances between each of the at least three marker elements, the assigning the rigid marker body geometry to the associated deformed navigable medical instrument, and the determining the positional relationship between the functional portion of the associated deformed navigable medical instrument and the reference array are performed when a landmark is generated by the associated deformed navigable medical instrument.

14. A non-transitory computer readable storable medium storing one or more sequences of instructions for automatically assigning identification to an associated navigable medical instrument in a medical navigation system operatively coupled with a tracking system, wherein said instructions, when executed by the tracking system or the medical navigation system, cause the one or more processors to execute steps of:
    storing first geometrical data in a non-transitory memory of the tracking system or the medical navigation system, the first geometrical data being representative of first physical properties of the navigable medical instrument at a first time before a use time of the navigable medical instrument;
    operating the tracking system at a second time before the use time to measure relative distances between each of at least three marker elements having a fixed mutual spatial relationship defining a rigid marker body geometry on a reference array coupled with the navigable medical instrument;
    assigning, by the tracking system or the medical navigation system, the reference array to the navigable medical instrument by associating in the non-transitory memory of the tracking system or the medical navigation system the measured relative distances with the first geometrical data of the navigable medical instrument;
    determining, by the tracking system, positional data representative of a position of the rigid marker body geometry relative to the tracking system, and providing the determined positional data to the medical navigation system;
    displaying on an output of the medical navigation system in accordance with the determined positional data an image of a position of the navigable medical instrument having the first physical properties and being assigned to the reference array;
    storing, at a third time after the use time of the navigable medical instrument, second geometrical data in the non-transitory memory of the tracking system or the medical navigation system, the second geometrical data being representative of second physical properties of the associated navigable medical instrument changed from the first physical properties to the second physical properties in accordance with the navigable medical instrument being deformed from the first physical properties to the second physical properties;
    operating the tracking system at a fourth time after the use time to re-measure the relative distances between each of the least three marker elements having the fixed mutual spatial relationship defining the rigid marker body geometry on the reference array coupled with the deformed navigable medical instrument;
    assigning, by the tracking system or the medical navigation system, the reference array to the deformed navigable medical instrument by associating in the non-transitory memory of the tracking system or the medical navigation system the re-measured relative distances with the second geometrical data of the deformed navigable medical instrument;
    determining, by the tracking system, positional data representative of a position of the rigid marker body geometry relative to the tracking system, and providing the positional data to the medical navigation system; and
    displaying on the output of the medical navigation system in accordance with the positional data an image of a position of the deformed navigable medical instrument having the second physical properties and being assigned to the reference array.

15. The non-transitory computer readable storable medium according to claim 14, wherein said instructions, when executed by the tracking system or the medical navigation system, cause the one or more processors to execute a further step of:
    re-measuring the relative distances between each of the at least three marker elements while one of the associated deformed navigable medical instrument or the tracking system is moved relative to the other of the associated deformed navigable medical instrument or the tracking system.

16. The non-transitory computer readable storable medium according to claim 14, wherein said instructions, when executed by the tracking system or the medical navigation system, cause the one or more processors to execute a further step of:
    determining a positional relationship between a functional portion of the associated deformed navigable medical instrument and the reference array by operating the tracking system to track the at least three marker elements as the associated deformed navigable medical instrument is moved while a tip of the associated navigable medical instrument remains at a spatially fixed location.

17. A system for automatically assigning identification to an associated navigable medical instrument, the system comprising:
    a medical navigation system;

a tracking system operatively coupled with the medical navigation system;

a processor and a non-transient computer readable medium, the processor and the non-transient computer readable medium being operatively coupled with the tracking system and the medical navigation system; and logic comprising one or more sequences of instructions stored in the memory, wherein said instructions, when executed by the tracking system or the medical navigation system, cause the one or more processors to execute steps of:

storing first geometrical data in a non-transitory memory of the tracking system or the medical navigation system, the first geometrical data being representative of first physical properties of the navigable medical instrument at a first time before a use time of the navigable medical instrument;

operating the tracking system at a second time before the use time to measure relative distances between each of at least three marker elements having a fixed mutual spatial relationship defining a rigid marker body geometry on a reference array coupled with the navigable medical instrument;

assigning, by the tracking system or the medical navigation system, the reference array to the navigable medical instrument by associating in the non-transitory memory of the tracking system or the medical navigation system the measured relative distances with the first geometrical data of the navigable medical instrument;

determining, by the tracking system, positional data representative of a position of the rigid marker body geometry relative to the tracking system, and providing the determined positional data to the medical navigation system;

displaying on an output of the medical navigation system in accordance with the determined positional data an image of a position of the navigable medical instrument having the first physical properties and being assigned to the reference array;

storing, at a third time after the use time of the navigable medical instrument, second geometrical data in the non-transitory memory of the tracking system or the medical navigation system, the second geometrical data being representative of second physical properties of the associated navigable medical instrument changed from the first physical properties to the second physical properties in accordance with the navigable medical instrument being deformed from the first physical properties to the second physical properties;

operating the tracking system at a fourth time after the use time to re-measure the relative distances between each of the least three marker elements having the fixed mutual spatial relationship defining the rigid marker body geometry on the reference array coupled with the deformed navigable medical instrument;

assigning, by the tracking system or the medical navigation system, the reference array to the deformed navigable medical instrument by associating in the non-transitory memory of the tracking system or the medical navigation system the re-measured relative distances with the second geometrical data of the deformed navigable medical instrument;

determining, by the tracking system, positional data representative of a position of the rigid marker body geometry relative to the tracking system, and providing the positional data to the medical navigation system; and displaying on the output of the medical navigation system in accordance with the positional data an image of a position of the deformed navigable medical instrument having the second physical properties and being assigned to the reference array.

18. The system for automatically assigning identification to an associated navigable medical instrument according to claim 17, wherein said instructions, when executed by the tracking system or the medical navigation system, cause the one or more processors to execute a further step of:

re-measuring the relative distances between each of the at least three marker elements while one of the associated deformed navigable medical instrument or the tracking system is moved relative to the other of the associated deformed navigable medical instrument or the tracking system.

19. The system for automatically assigning identification to an associated navigable medical instrument according to claim 17, wherein said instructions, when executed by the tracking system or the medical navigation system, cause the one or more processors to execute a further step of:

determining a positional relationship between a functional portion of the associated deformed navigable medical instrument and the reference array by operating the tracking system to track the at least three marker elements as the associated deformed navigable medical instrument is moved while a tip of the associated deformed navigable medical instrument remains at a spatially fixed location.

* * * * *